United States Patent [19]

Greenleaf et al.

[11] Patent Number: 5,348,730
[45] Date of Patent: Sep. 20, 1994

[54] METHOD FOR PREPARING MEDICINAL AEROSOL FORMULATION CONTAINING COATED MEDICAMENT

[75] Inventors: David J. Greenleaf, Loughborough; Tarlochan S. Purewal, Leamington Spa; Philip A. Jinks, Mount Sorrel, all of Great Britain

[73] Assignee: Minnesota Mining and Manufacturing Company, St. Paul, Minn.

[21] Appl. No.: 838,747

[22] PCT Filed: Sep. 20, 1990

[86] PCT No.: PCT/GB90/01454
§ 371 Date: Mar. 17, 1992
§ 102(e) Date: Mar. 17, 1992

[87] PCT Pub. No.: WO90/07333
PCT Pub. Date: Jul. 12, 1990

[30] Foreign Application Priority Data

Sep. 20, 1989 [GB] United Kingdom ............... 8921222

[51] Int. Cl.$^5$ ..................... A61K 9/12; A61K 9/72
[52] U.S. Cl. ......................... 424/45; 424/43; 424/46; 424/489; 424/490; 424/498; 427/2.14; 514/951; 514/975
[58] Field of Search ............ 424/43, 45, 46, 489, 424/490, 498; 514/951, 975; 427/2

[56] References Cited

U.S. PATENT DOCUMENTS

| | | | |
|---|---|---|---|
| 3,014,844 | 12/1961 | Thiel et al. | 424/46 |
| 4,174,295 | 11/1979 | Bargigia et al. | 252/305 |
| 4,352,789 | 10/1982 | Thiel | 424/46 |
| 4,520,142 | 5/1985 | Leinen | 523/205 |
| 4,849,427 | 7/1989 | Nassim et al. | 514/291 |
| 5,141,674 | 8/1992 | Leigh | 252/305 |

FOREIGN PATENT DOCUMENTS

| | | |
|---|---|---|
| 372777A2 | 6/1990 | European Pat. Off. |
| 1719443 | 4/1972 | Fed. Rep. of Germany |
| 837465 | 6/1960 | United Kingdom |
| 977934 | 12/1964 | United Kingdom |
| 1063512 | 3/1967 | United Kingdom |
| 2001334 | 1/1979 | United Kingdom |
| 90/07333 | 1/1990 | PCT Int'l Appl. |

Primary Examiner—Thurman K. Page
Assistant Examiner—Robert H. Harrison
Attorney, Agent, or Firm—Gary L. Griswold; Walter N. Kirn; Douglas E. Reedich

[57] ABSTRACT

A method for preparing a self-propelling, powder dispersing aerosol composition comprising at least 0.0001% by weight of a finely-divided solid medicament coated with a non-perfluorinated surface active dispersing agent which constitutes at least 0.0001% by weight of the coated solid material, and suspended in an aerosol propellant in which the non-perfluorinated surface-active dispersing agent is substantially insoluble. Propellant-insoluble non-perfluorinated surfactants are used to prepare stable dispersions of powdered medicament by way of pre-coating the medicament with the surfactant prior to admixture with propellant.

8 Claims, No Drawings

METHOD FOR PREPARING MEDICINAL AEROSOL FORMULATION CONTAINING COATED MEDICAMENT

This invention relates to medicinal aerosol formulations and in particular to formulations suitable for pulmonary, nasal, buccal or topical administration which are at least substantially free of chlorofluorocarbons.

Since the metered dose pressurized inhaler was introduced in the mid 1950's, inhalation has become the most widely used route for delivering bronchodilator drugs and steroids to the airways of asthmatic patients. Compared with oral administration of bronchodilators, inhalation offers a rapid onset of action and a low instance of systemic side effects. More recently, inhalation from a pressurized inhaler has been a route selected for the administration of other drugs, e.g., ergotamine, which are not primarily concerned with the treatment of a bronchial malady.

The metered dose inhaler is dependent upon the propulsive force of a propellant system used in its manufacture. The propellant generally comprises a mixture of liquified chlorofluorocarbons (CFC's) which are selected to provide both the desired vapour pressure and stability of formulation. Propellants 11, 12 and 114 are the most widely used propellants in aerosol formulations for inhalation administration.

In recent years it has been established that CFC's react with the ozone layer around the earth and contribute towards its depletion. There has been considerable pressure around the world to reduce substantially the use of CFC's, and various Governments have banned the "non-essential" use of CFC's. Such "non-essential" uses include the use of CFC's as refrigerants and blowing agents, but heretofore the use of CFC's in medicines, which contributes to less than 1% of the total use of CFC's, has not been restricted. Nevertheless, in view of the adverse effect of CFC's on the ozone layer it is desirable to seek alternative propellant systems which are suitable for use in inhalation aerosols.

Our copending European Patent Application No. 89312270.5 discloses an aerosol formulation comprising a medicament, a surfactant, 1,1,1,2-tetrafluoroethane and at least one compound having a higher polarity than 1,1,1,2-tetrafluoroethane.

It is disclosed that 1,1,1,2-tetrafluoroethane, hereinafter referred to as Propellant 134a, may be employed as a propellant for aerosol formulations suitable for inhalation therapy when used in combination with a compound having a higher polarity than Propellant 134a. Suitable compounds include alcohols such as ethyl alcohol, isopropyl alcohol, propylene glycol, hydrocarbons such as propane, butane, isobutane, pentane, isopentane, neopentane, and other propellants such as those commonly referred to as Propellants 11, 12, 114, 113, 22, 142b, 152a, 124 and dimethyl ether. The combination of one or more of such compounds with Propellant 134a provides a propellant system which has comparable properties to those of propellant systems based on CFC's, allowing use of known surfactants and additives in the pharmaceutical formulations and conventional valve components. This is particularly advantageous since the toxicity and use of such compounds in metered dose inhalers for drug delivery to the human respiratory tract is well established.

Non-perfluorinated surfactants have commonly been used as dispersing agents for powdered medicaments in aerosol propellants in which the non-perfluorinated surfactants are soluble. Examples of such aerosol formulations are disclosed in British Patents Nos. 837465, 977934, 1063512, 2001334 and US Pat. No. 4,352,789. However, many of these non-perfluorinated surfactants are substantially insoluble in Propellant 134a and other propellants which are being considered as replacements for chlorofluorocarbon aerosol propellants i.e., a ordinary room temperature it requires more than 10,000 parts of propellant to dissolve 1 part of surfactant.

It has been found that non-perfluorinated surfactants which are insoluble in a propellant may nevertheless be used with such a propellant to form stable dispersions of powdered medicament provided the powdered medicament is pre-coated with the non-perfluorinated surfactant prior to dispersing the powdered medicament in the propellant.

Therefore according to the invention there is provided a self-propelling, powder dispensing aerosol composition comprising at least 0.001% by weight of a finely-divided solid medicament coated with a non-perfluorinated surface,-active dispersing agent which constitutes at least 0.001% and generally to 20% by weight of the coated solid medicament, and suspended in an aerosol propellant in which the non-perfluorinated surface-active dispersing agent is substantially insoluble.

It has been found that non-perfluorinated surfactants, which have previously been used as dispensing agents for powdered medicaments in propellants in which the non-perfluorinated surfactant is soluble, may be used to form stable dispersions of powdered medicament in propellants in which the non-perfluorinated surfactant is insoluble provided the medicament is precoated with the surfactant prior to dispensing in the propellant. This result is particularly surprising in view of the fact that the same stable dispersions cannot be achieved by simple admixture of the surfactant, propellant and medicament.

The invention is particularly useful in that it allows acceptably stable dispersions to be attained using Propellant 134a as the aerosol propellant. The formulations of the invention may be prepared with Propellant 134a alone or a mixture of Propellant 134a and another miscible adjuvant having a polarity equal to or lower than the polarity of Propellant 134a. Suitable adjuvants for use with Propellants 134a include perfluorinated organic compounds such as perfluorinated alkanes and cycloalkanes. Specific examples of adjuvants include those shown in the following Table.

| Name | Chemical Formula | Vapor Pressure at 20° C. (psig) | Boiling Point (°C.) | Density (g/ml) |
| --- | --- | --- | --- | --- |
| perfluoropropane | $C_3F_8$ | 100 | −37 | 1.6 |
| perfluorobutane | $C_4F_{10}$ | −3 | 20 | — |
| perfluorocyclobutane | $C_4F_8$ | 25 | −6 | 1.48 |
| perfluoropentane | $C_5F_{12}$ | −3 | +29 | 1.62 |
| perfluorohexane | $C_6F_{14}$ | — | 54–58 | 1.68 |

-continued

| Name | Chemical Formula | Vapor Pressure at 20° C. (psig) | Boiling Point (°C.) | Density (g/ml) |
| --- | --- | --- | --- | --- |
| perfluorotributylamine | $(C_4F_9)_3N$ | — | 70 (12 mm Hg) | 1.90 |
| perfluoromethylcyclohexane | $C_7F_{14}$ | — | 76 | 1.80 |
| perfluorodecalin | $C_{10}F_{18}$ | — | 140–142 | 1.94 |

Adjuvants having a lower boiling point which contribute towards the propellant system are preferred. The most preferred adjuvant is perfluoropentane. Preferred propellant systems comprise from 5 to 50% by weight of adjuvant and 50 to 95% by weight of Propellant 134a.

Polarity of adjuvants may be measured using the Kauri-butanol value for estimation of solvent power. The protocol is described in ASTM Standard: Designation 1133-86. However, the scope of the aforementioned test method is limited to hydrocarbon solvents having a boiling point over 40° C. The method has been modified as described below for applications to more volatile substances such as required for propellant.

Standardization

In conventional testing the Kauri resin solution is standardized against toluene, which has an assigned value of 105 and a mixture of 75% n-heptane and 25% toluene by volume which has an assigned value of 40. When the sample has a Kauri-butanol value lower than 40, it is more appropriate to use a single reference standard of 75% n-heptane: 25% toluene. The concentration of Kauri-butanol solution is adjusted until a titer between 35 ml and 45 ml of the reference standard is obtained by the method of the ASTM standard providing the adjuvant is non-volatile.

Method for Volatile Compounds

The density of the volatile substance under test is calculated to allow a volumetric titration from the added weight of the sample after testing.

Kauri-butanol solution (20 g) was weighed into an aerosol bottle. A non-metering value was crimped onto the bottle and the weight of bottle and sample measured. Following the procedure detailed in ASTM standards as closely as possible, successive amounts of the volatile sample were transferred from an aerosol bottle via a transfer button until the end point was reached (as defined in ASTM). The aerosol bottle with titrated Kauri-butanol solution was re-weighed.

The Kauri-butanol value is calculated using the following formula:

$$V = \frac{(W_2 - W_1)}{d} \times \frac{40}{B}$$

in which:
$W_2$ = weight of aerosol bottle after titration (g)
$W_1$ = weight of aerosol bottle before titration (g)
d = density of sample (g/ml)
B is as defined in the ASTM standard = ml of heptane-toluene blend required to titrate 20 g of Kauri-butanol solution.

If a titer (V) is obtained by precipitation of the Kauri resin out of solution, then a higher Kauri-butanol represents a sample of higher polarity.

If the sample and Kauri-butanol solution are immiscible, this is most likely due to immiscibility of the sample with butanol due to excessively low polarity. However, it is feasible that excessively high polarity could result in immiscibility. This is tested by checking the miscibility of the sample with water. If the sample is immiscible with water and immiscible with Kauri-butanol solution, then the Kauri-butanol value is deemed too low to be measured, and the polarity is to be regarded as lower than that of any material which would give a proper titer into Kauri-butanol solution.

The propellant system comprising Propellant 134a and perfluoropentane possesses particular advantages since it is readily possible to formulate mixtures having a wide range of densities to suit different drugs while maintaining a substantially constant vapor pressure for the mixtures of about 65psig at 20° C. Such a mixture exhibits an azeotrope with quite a high percentage of the less volatile component, perfluoropentane, for example, perfluoropentane may be present in an amount as high as 50% by weight, preferably in the range 20 to 40% by weight of the propellant mixtures.

The invention is not limited to the use of Propellant 134a in the propellant system and may employ any propellant in which the dispersing agent is substantially insoluble. Other useful propellants include certain halocarbons, particularly perfluorinated hydrocarbons, hydrocarbons and admixtures alchohol.

Suitable dispersing agents for use in the invention comprise non-perfluorinated surfactants which have been used in inhalation formulations with propellants other than Propellant 134a. Examples of suitable dispersing agents include: oils derived from natural sources, such as, corn oil, olive oil, cotton seed oil and sunflower seed oil.

Sorbitan trioleate available under the trade name Span 85,
Sorbitan mono-oleate available under the trade name Span 80,
Sorbitan monolaurate available under the trade name Span 20,
Polyoxyethylene (20) sorbitan monolaurate available under the trade name Tween 20,
Polyoxyethylene (20) sorbitan mono-oleate available under the trade name Tween 80,
lecithins derived from natural sources such as those available under the trade name Epikuron particularly Epikuron 200.
Oleyl polyoxyethylene (2) ether available under the trade name Brij 92,
Stearyl poloxyethylene (2) available under the trade name Brij 72,
Lauryl polyoxyethylene (4) ether available under the trade name Brij 30,
Oleyl polyoxyethylene (2) ether available under the trade name Genapol 0-020,
Block copolymers of oxyethylene and oxypropylene available under the trade name Synperonic,
Oleic acid, Synthetic lecithin, Diethylene glycol dioleate, Tetrahydrofurfuryl oleate, Ethyl oleate, Isopropyl myristate, Glyceryl trioleate, Glyceryl monolaurate, Glyceryl mono-oleate, Glyceryl monostearate, Glyceryl monoricinoleate, Cetyl alcohol, Stearyl alcohol, Polyethylene glycol 400, Cetyl pyridinium chloride.

The non-perfluorinated surfactant consitutes at least 0.001% to generally 0.001 to 20% more generally between 0.001 and 5%, and preferably, for medicinal purposes, between 0,001 and 3% by weight of the solid material to be suspended. However, the minimum amount of surfactant required is dependent upon the concentration of solid material present. For best results, the concentration of surface-active agent is kept at a minimum as it may tend to increase the droplet size and the tendency for particle agglomeration.

Suitable solid medicaments include antiallergics, analgesics, bronchodilators, antihistamines, thereapeutic proteins and peptides, antitussives, anginal preparations, antibiotics, antiinflammatory preparations, hormones, or sulfonamides, such as, for example, a vasoconstrictive amine, an enzyme, alkaloid, or steroid, and synergistic combinations of these. Examples of medicaments which may be employed are: Isoproterenol [alpha-(isopropylaminomethyl) protocatechuyl alcohol], phenylephrine, phenylpropanolamine, glucagon, adrenochrome, trypsin, epinephrine, ephedrine, narcotine, codeine, atropine, heparin, morphine, dihydromorphinone, ergotamine, scopolamine, methapyrilene, cyanocobalamin, terbutaline, rimiterol, salbutamol, flunisolide, colchicine, pirbuterol, beclomethasone, orciprenaline, fentanyl, and diamorphine. Others are antibiotics, such as neomycin, streptomycin, penicillin, procaine penicillin, tetracycline, chlorotetracycline and hydroxytetracycline; adrenocorticotropic hormone and adrenocortical hormones, such as cortisone, hydrocortisone, hydrocortisone acetate and prednisolone; insulin, antiallergy compounds such as cromolyn sodium, etc.

The drugs exemplified above may be used as either the free base or as one or more salts known to the art. The choice of free base or salt will be influenced by the physical stability of the drug in the formulation. For example, it has been shown that the free base of salbutamol exhibits a greater dispersion stability than salbutamol sulphate in the formulations of the invention.

The following salts of the drugs mentioned above may be used;

acetate, benzenesulphonate, benzoate, bicarbonate, bitartrate, bromide, calcium edetate, camsylate, carbonate, chloride, citrate, dihydrochloride, edetate, edisylate, estolate, esylate, fumarate, fluceptate, gluconate, glutamate, glycollylarsanilate, hexylresorcinate, hydrobromide, hydrochloride, hydroxynaphthoate, iodide, isethionate, lactate, lactobionate, malate, maleate, mandelate, mesylate, methylbromide, methylnitrate, methylsulphate, mucate, napsylate, nitrate, pamoate (embonate), pantothenate, phosphate diphosphate, polygalacturonate, salicylate, stearate, subacetate, succinate, sulphate, tannate, tartrate, and triethiodide.

Cationic salts may also be used. Suitable cationic salts include the alkali metals, e.g. sodium and potassium, and ammonium salts and salts of amines known in the art to be pharmaceutically acceptable, e.g. glycine, ethylene diamine, choline, diethanolamine, triethanolamine, octadecylamine, diethylamine, triethylamine, 1-amino-2-propanol-amino-2-(hydroxymethyl)propane-1,3-diol and 1-(3,4-dihydroxyphenyl)-2 isopropylaminoethanol.

Preferred drugs for the invention are salbutamol, salbutamol sulphate, beclomethasone diproprionate isopropylacohol solvate, sodium cromoglycate, pirbuterol, pirbuterol acetate, beclomethasone dipropionate and fentanyl citrate.

For pharmaceutical purposes the particle size of the powder should desirably be no greater than 100 microns diameter, since larger particles may tend to agglomerate, separate from the suspension may clog the valve or orifice of the container. Preferably the particle size should be less than 25 microns in diameter. Desirably the particle size of the finely-divided solid powder should for physiological reasons be less than 25 microns and preferably less than about 10 microns in diameter. The particle size of the powder for inhalation therapy should preferably be in the range 2 to 10 microns.

There is no lower limit on particle size except that imposed by the use to which the aerosol produced is to be put. Where the powder is a solid medicament, the lower limit of particle size is that which will be readily absorbed and retained on or in body tissues. When particles of less than about one-half micron in diameter are administered by inhalation they tend to be exhaled by the patient.

Desirably the finely divided solid materials should be substantially insoluble in both the liquified propellant and the surface-active agent. If the solid material is substantially soluble in the propellant, the particle size of the aerosolized material when dispensed cannot be controlled. If the particle size of the suspended solid material cannot be regulated and agglomeration takes place, the valve orifice of the aerosol container may clog, rendering the dispensing device inoperative, or if a metering valve is employed, it may be rendered inaccurate. This may lead to inaccurate dosages, which in the case of highly potent medicinals may lead to undesirable results. In addition to increasing particle size and clogging orifices, agglomeration may make the suspension unstable, an obviously undesirable result, particularly in the case of aerosolized medicinals.

The finely-divided solid material may constitute up to about 20% by weight of the total composition. Generally it will constitute up to 10%, normally up to 5% and preferably up to 3%, by weight of the total composition. The minimum concentration of the solid material is governed by its specific activity and in the case of highly active material can be as low as 0.001% by weight of the total composition although a concentration of 0.01% is preferred.

The invention will now be described with reference to the following Examples in which formulations of the invention are prepared according to the following general method.

Method for Coating Drug Particles with Surfactant and Preparations of Formulations A solution of surfactant is prepared in a solvent in which the selected drug is either insoluble or has a suitably low solubility. The concentration, of the surfactant solution varies with the selected drug but is typically less than 10% (w/v) and more usually in the range 0.001 to 5% (w/v). An appropriate quantity of the surfactant solution is mixed with the micronized drug powder for 1 minute using a high shear mixer in accordance with techniques known to the art. Micronized drug powder is defined as comprising particles having a size distribution of 95% of particles below 10 um and a mean size in the range of 1 to 5 um. After mixing, the drug particles are coated with a layer of surfactant. Coated particles are separated from the suspension by filtration and dried. The powder is collected and deaggregated to produce a free flowing powder.

The appropriate quantity of the coated drug and propellant are then admixed in a suitable container and subjected to high energy dispersion, e.g. ultrasonic energy has been found to be effective at this stage. This technique has been demonstrated to be effective in physically stabilizing suspension formulations.

EXAMPLE 1

Method for Determining the Drug Deposition Potential of the Formulations

The formulations were evaluated by the following protocol to demonstrate the improvement brought about by coating the micronized drug particles with a suitable surfactant in accordance with the invention. The quantification of the improvement was expressed as the drug deposition potential of a given formulation and was determined as follows:

(a) The surfactant coated drug was prepared as described above from micronized drug in dehumidified conditions. The control comprising the same formulation but omitting the surfactant was subjected to the same procedure.

(b) 69 mg of the coated drug (or control) was added to each of several 10 ml capacity aluminium aerosol cans. Polyethylene terephthalate (PET) aerosol containers may be substituted where appropriate. An aerosol valve was crimped into place before addition of Propellant 134a (7.9 g). Once crimping had been effected cans could be removed from the dehumidified environment.

(c) The contents of each can were homogenized by immersion in an ultrasonic bath for five minutes.

(d) The cans were subjected to the following conditions, designed to promote drug deposition:

Each can was placed on its side on an electric rolling apparatus such that it is in a position to rotate about an axis parallel with its axis of rotational symmetry, i.e. its longitudinal axis. The apparatus was programmed to be alternately switched on for 15 minutes and then off for 15 minutes, for a total of 15 hours operation time (30 cycles).

Each can subjected to intermittent rolled storage was chilled for 30 minutes at −50° C.

Immediately prior to decrimping the valve, the can was inverted to ensure that undeposited drug particles are dispersed. The valve was decrimped and the can contents discarded.

(e) The deposits from each can were rinsed with a suitable solvent, ensuring quantitative transfer of the washings, into a volumetric flask. Where appropriate the flask contents were made up to the required volume with solvent, before u.v. spectrophotometric analysis of the drug. Where necessary samples were diluted to provide an absorbance within the linear range of the Beer-Lambert Law.

(f) The amount of drug deposited from each preparation (including the control) was determined and the results expressed as follows:

$$\text{Drug Deposition Potential} = \frac{\text{Average weight of drug deposits from test formulation}}{\text{Average weight of drug deposits from control formulation}}$$

A value of less than 1.0 for the drug deposition potential indicates an improvement due to the pre-coating of the micronized drug particles with the surfactant. The following preparations were examined and the results presented in the following table.

| Formulation | Drug | Surfactant | Concentration of surfactant in the coating Solution (% w/v) | Container type | Drug Deposition* Potential |
|---|---|---|---|---|---|
| 1 | Beclomethasone Dipropionate (1) | Epikuron 200 | 0.001 | Aluminum | 0.64 |
| 2 | Betamethasone | Epikuron 200 | 0.100 | PET | 0.45 |
| 3 | Betamethasone | Epikuron 200 | 0.100 | PET | 0.57 |
| 4 | Ergotamine Tartrate | Epikuron 200 | 0.100 | PET | 0.36 |
| 5 | Salbutamol Sulphate | Span 85 | 0.100 | Aluminum | 0.60 |
| 6 | Sodium Cromoglycate B.P. | Epikuron 200 | 0.100 | PET | 0.76 |
| 7 | Salbutamol B.P. | Epikuron 200 | 0.100 | Aluminum | 0.92 |
| 8 | Salbutamol Sulphate B.P. | Epikuron 200 | 0.020 | Aluminum | 0.85 |

*a mean of multiple determination on separate cans
(1) isopropyl alcohol solvate

EXAMPLE 2

Demonstration of the Advantage of Pre-Coating the Drug Particles Compared with an Admixture of the Constituents The formulations of the invention cannot be arrived at by simply mixing ingredients and agitating the mixture in a conventional manner. This conclusion is based on the following results:

(1) Addition of a surfactant to Propellant 134a in a chilled vessel causes the surfactant to gel or solidify and collect in an undissolved mass.

(2) The following preparation was prepared using ultrasonic energy to homogenise in a sealed a container of mixture (A)

| | mg/ml |
|---|---|
| Beclomethasone Dipropionate (I.P.A. solvate) | 10.700 |
| Epikuron 200 | 0.027 |
| Propellant 134a | 1214.273 |
| TOTAL | 1225.000 |

The above mixture has the same ingredients as formulation 1 of Example 1. The drug deposition potential of the mixture was evaluated and the results reported in the table below.

The results of Formulation 1 are included as comparative data.

| | Drug Deposition Potential* | | |
|---|---|---|---|
| Formulation 1 (pre-coated drug) | 0.62 | 0.76 | 0.53 |
| Formulation A (admixed drug and surfactant) | 1.89 | 1.51 | 1.32 |

*Each result represents a determination on a separate can.

It can be seen from the formulations tested that those formulations prepared using pre-coated drug are better than both those containing no surfactant (see (1) above) and the formulation prepared in the conventional way (Formulation A) by simply admixing the constituents.

EXAMPLE 3

This example demonstrates that drug formulations may be prepared using a mixture of propellant 134a and an adjuvant/propellant of polarity equal to or less than the polarity of Propellant 134a. Formulations have been prepared in accordance with the following general formula:

| | mg/ml |
|---|---|
| Salbutamol B.P. (micronized and pre-coated with surfactant) | 2.0 |
| Propellant 134a | 1030.0 |
| Perfluoropentane | 258.0 |
| TOTAL | 1290.0 |

Satisfactory formulations have been prepared where the surfactant used to pre-coat the salbutamol was;
 (a) Span 85
 (b) Oleic acid B.P., and
 (c) Epikuron 200

The above formulations were prepared by dispersing the pre-coated drug particles in perfluoropentane before addition of Propellant 134a.

Furthermore, substitution of uncoated drug for the pre-coated drug resulted in unsatisfactory preparations, in which, most of the uncoated drug stuck to the walls of the homogenizing vessel and did not disperse adequately.

EXAMPLE 4

Formulations containing micronized Salbutamol B.P.

The suspension formulations reported in the following Table were prepared as described above.

| Formulation Number | Surfactant Coated Drug Particles (g) | Propellant 134a (g) | Surfactant used to coat the drug particles | Concentration of surfactant in the coating solution (%) |
|---|---|---|---|---|
| SS1 | 0.02 | 12.2 | Span 85 | 0.1 |
| SS2 | 0.02 | 12.2 | Span 85 | 5.0 |
| SO1 | 0.02 | 12.2 | Oleic Acid | 0.1 |
| SO2 | 0.02 | 12.2 | Oleic Acid | 1.0 |
| SE1 | 0.02 | 12.2 | Epikuron 200 | 0.1 |
| SE2 | 0.02 | 12.2 | Epikuron 200 | 5.0 |

Of the above formulations, Formulation SE2 was the most satisfactorily dispersed.

EXAMPLE 5

Formulations containing micronized Pirbuterol acetate

The suspension formulations reported in the following Table were prepared as described above:

| Formulation Number | Surfactant Coated Drug Particles (g) | Propellant 134a (g) | Surfactant used to coat the drug particles | Concentration of surfactant in the coating solution (%) |
|---|---|---|---|---|
| PS1 | 0.05 | 12.2 | Span 85 | 0.1 |
| PS2 | 0.05 | 12.2 | Span 85 | 5.0 |
| PO1 | 0.05 | 12.2 | Oleic Acid | 0.1 |
| PO2 | 0.05 | 12.2 | Oleic Acid | 1.0 |
| PE1 | 0.05 | 12.2 | Epikuron 200 | 0.1 |
| PE2 | 0.05 | 12.2 | Epikuron 200 | 5.0 |

EXAMPLE 6

Formulations containing micronized adrenaline bitartrate

The suspension formulations reported in the following Table were prepared as described above.

| Formulation Number | Surfactant Coated Drug Particles (g) | Propellant 134a (g) | Surfactant used to coat the drug particles | Concentration of surfactant in the coating solution (%) |
|---|---|---|---|---|
| AS1 | 0.056 | 12.2 | Span 85 | 0.1 |
| AS2 | 0.056 | 12.2 | Span 85 | 5.0 |
| AO1 | 0.056 | 12.2 | Oleic Acid | 0.1 |
| AO2 | 0.056 | 12.2 | Oleic Acid | 1.0 |
| AE1 | 0.056 | 12.2 | Epikuron 200 | 0.1 |
| AE2 | 0.056 | 12.2 | Epikuron 200 | 5.0 |

Of the above formulations, Formulation AE2 was the most satisfactorily dispersed.

EXAMPLE 7

Formulations containing micronized Salbutamol B.P. with perfluoropropane

The suspension formulations reported in the following Table were prepared as described above.

| Formulation Number | Surfactant Coated Drug Particles (g) | Perfluoropropane (g) | Surfactant used to coat the drug particles | Concentration of surfactant in the coating solution (%) |
|---|---|---|---|---|
| PF1 | 0.02 | 12.2 | Span 85 | 0.1 |
| PF2 | 0.02 | 12.2 | Span 85 | 5.0 |
| PF3 | 0.02 | 12.2 | Oleic Acid | 0.1 |
| PF4 | 0.02 | 12.2 | Oleic Acid | 1.0 |
| PF5 | 0.02 | 12.2 | Epikuron 200 | 0.1 |
| PF6 | 0.02 | 12.2 | Epikuron 200 | 5.0 |

The claimed invention is:

1. A method for preparing an aerosol composition comprising:
 a) coating a finely divided solid drug with non-perfluorinated surface-active dispersing agent in a solvent in which the finely divided solid drug is substantially insoluble to afford a coated solid medicament,
 (b) separating the coated solid medicament from the solvent,
 (c) drying the coated solid medicament, (d) dispersing the coated solid medicament in an aerosol propellant substantially free of chlorofluorocarbons and in which the surface active dispersing agent is substantially insoluble such that the aerosol composition comprises from 0,001% to 20% by weight of said coated solid medicament and 0,001% to 50% by weight of the coated solid medicament is the non-perfluorinated surface-active dispersing agent.

2. A method according to claim 1, wherein the finely-divided solid medicament of step (a) has an average particle size of less than 10 microns in diameter.

3. A method according to claim 1, wherein the dispersing agent of step (a) is selected from the group consisting of sorbitan trioleate, sorbitan mono-oleate, sorbitan monolaurate, polyoxyethylene (20) sorbitan monolaurate, polyoxyethylene (20) sorbitan mono-oleate, natural lecithin, oleyl polyoxyethylene (2) ether, stearyl polyoxyethylene (2) ether, lauryl polyoxyethylene (4) ether, block copolymers of oxyethylene and oxypropylene, Oleic acid, Synthetic lecithin, Diethylene glycol dioleate, Tetrahydrofurfuryl oleate, Ethyl oleate, Isopropyl myristate, Glyceryl mono-oleate, Glyceryl monostearate, Glyceryl monoricinoleate, Cetyl alcohol, Stearyl alcohol, Polyethylene glycol 400 and Cetyl pyridinium chloride, olive oil, glyceryl monolaurate, corn oil, cotton seed oil and sunflower seed oil.

4. A method according to claim 1, wherein the finely divided solid medicament of step (a) comprises a drug selected from the group consisting of an antiallergic, an analgesic, a bronchodilator, an antihistamine, a steroid, an antitussive, an anginal preparation, an antibiotic, an antiinflammatory, a hormone, a sulfonamide, and a therapeutic protein or peptide.

5. A method according to claim 4, wherein the drug is selected from the group consisting of salbutamol and its salts, beclomethasone dipropionate, pirbuterol and its salts, adrenaline and its salts, and disodium cromoglycate.

6. A method according to claim 1, wherein the propellant of step (d) comprises 1,1,1,2-tetrafluoroethane.

7. A method according to claim 6, wherein the propellant of step (d) further comprises an adjuvant selected from the group consisting of perfluoropropane, perfluorobutane, octafluorocyclobutane, perfluoropentane, perfluorohexane, perfluorotributylamine, perfluoromethylcyclohexane and perfluorodecalin.

8. A method according to claim 7, wherein the propellant of step (d) comprises from 5 to 50% by weight of adjuvant and from 50 to 95% by weight of 1,1,1,2-tetrafluoroethane.

* * * * *

UNITED STATES PATENT AND TRADEMARK OFFICE
CERTIFICATE OF CORRECTION

PATENT NO. : 5,348,730
DATED : September 20, 1994
INVENTOR(S) : David J. Greenleaf et al.

It is certified that error appears in the above-indentified patent and that said Letters Patent is hereby corrected as shown below:

Col. 11, line 5, "0,001%" should be --0.001%--.

Col. 11, line 7, "0,001%" should be --0.001%--.

Signed and Sealed this

Fourth Day of April, 1995

Attest:

BRUCE LEHMAN

Attesting Officer          Commissioner of Patents and Trademarks